United States Patent [19]

Bark et al.

[11] Patent Number: 5,066,303
[45] Date of Patent: Nov. 19, 1991

[54] SELF-SEALING TISSUE EXPANDER AND METHOD

[75] Inventors: Jeffrey E. Bark, Racine; Donald V. Hillegass, Franksville; Eric J. Woodruff, Racine, all of Wis.

[73] Assignee: Medical Engineering Corporation, Racine, Wis.

[21] Appl. No.: 390,267

[22] Filed: Aug. 7, 1989

[51] Int. Cl.⁵ .............................................. A61F 2/12
[52] U.S. Cl. ..................................................... 623/8
[58] Field of Search ........................... 623/7, 8, 11, 12

[56] References Cited

U.S. PATENT DOCUMENTS 4,428,364 1/1984 Bantolo .................................. 623/8

Primary Examiner—David J. Isabella
Attorney, Agent, or Firm—Stuart E. Krieger

[57] ABSTRACT

The self-sealing tissue expander includes inner and outer layers of relatively nonflowable material and a median layer of flowable material, The median layer of flowable material which can include one or more sublayers of flowable material is under a predetermined compression imposed by the inner and outer layers due to a prestressing of the tissue expander shell during formation of the tissue expander. The self-sealing shell seals an opening in the shell wall following removal of an infusion needle. In all embodiments of the invention a needle stop member is provided to prevent the needle that accesses the fluid chamber from passing outwardly of the tissue expander. The need for a septum, a fluid conduit or a special fluid entry opening in the tissue expander shell is thus optional. The shell can also be made relatively more stretchable in some areas than in other areas.

39 Claims, 4 Drawing Sheets

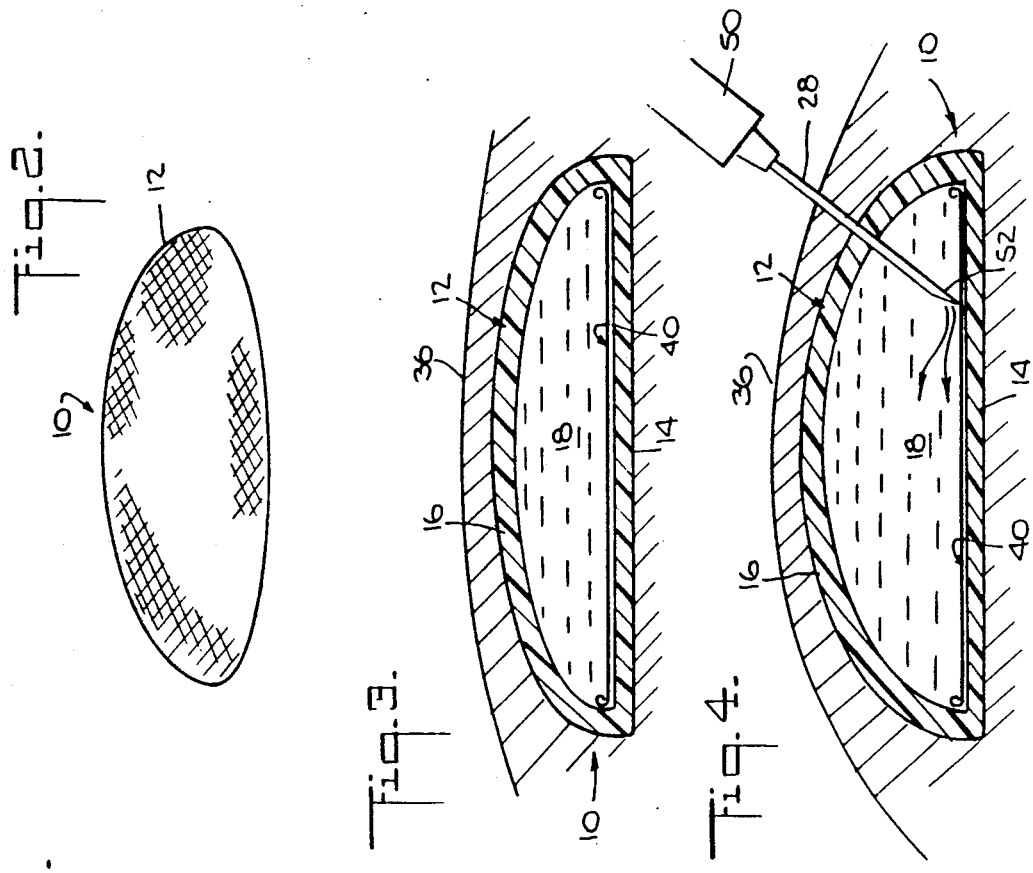
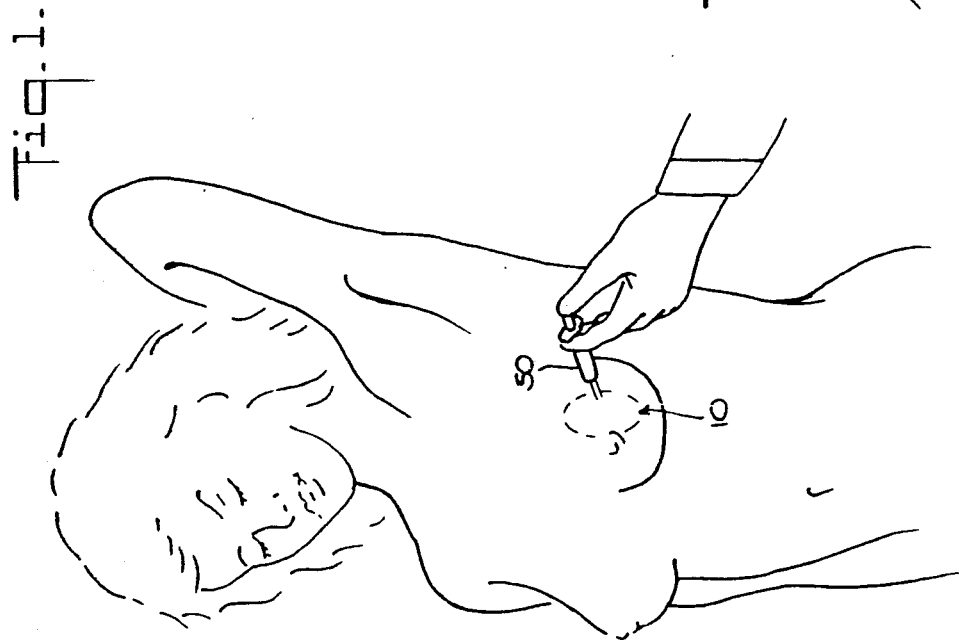

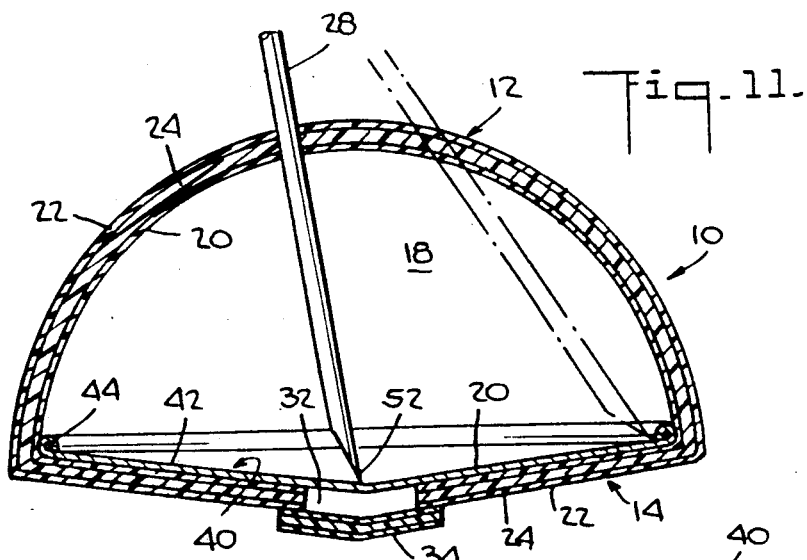
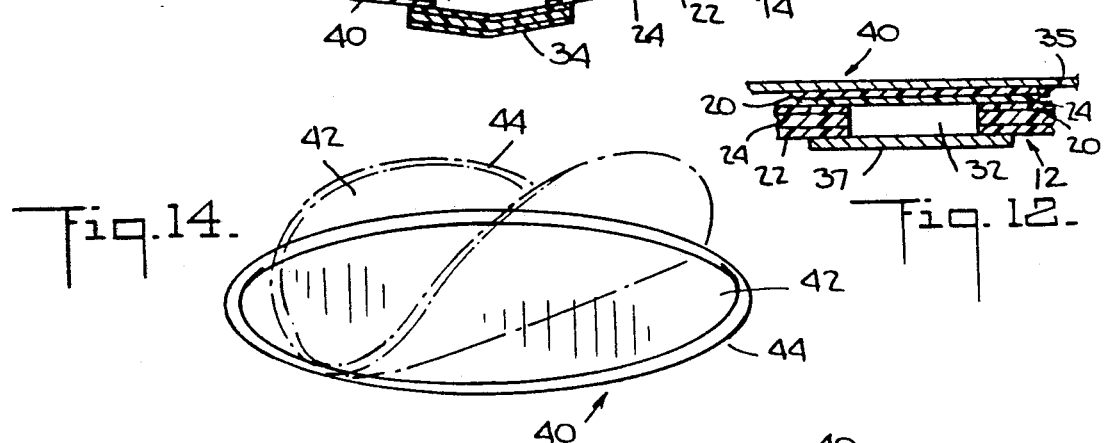
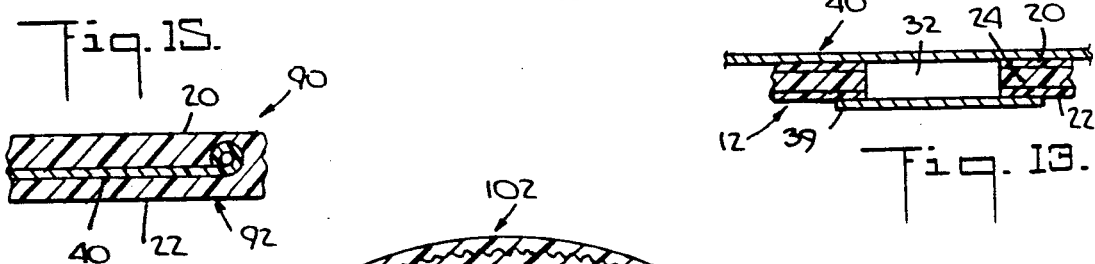
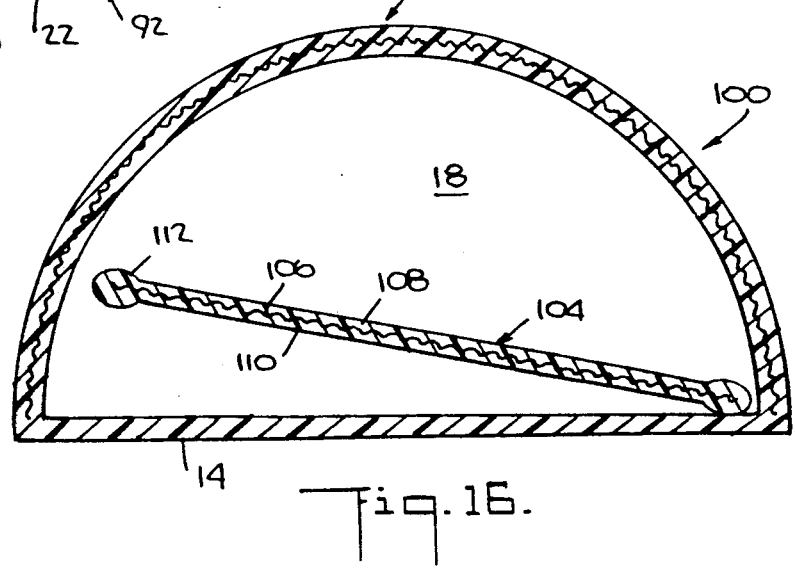

SELF-SEALING TISSUE EXPANDER AND METHOD

BACKGROUND OF THE INVENTION

This invention relates to implantable devices which can be infused with fluid for promoting tissue growth or tissue expansion, and more particularly to a flexible, foldable, fluid expandable prosthetic device that can be directly infused by a needle and is self sealing when the needle is removed.

The promotion of tissue growth or tissue expansion, as for example, in a mammary prosthesis, is generally based on a gradual accumulation of fluid in an expansible fluid containing device or prosthesis. The prosthesis is typically a collapsible shell formed of a flexible, foldable material which establishes a fluid chamber. Periodic infusions of fluid are made into the fluid chamber to develop a gradual expansion of the surrounding shell. As a result of such periodic infusions of fluid, the tissue which overlies the prosthesis expands or grows accordingly.

Infusion of fluid into a tissue expander prosthesis is normally accomplished with an infusion needle. Since a tissue expander shell is likely to leak if punctured by a needle, it is common practice to infuse fluid at a location that is remote from the tissue expander shell. A tissue expander system thus generally includes a remote needle penetrable septum such as shown in U.S. Pat. Nos. 4,190,040; 4,463,733; 4,543,088 and 4,685,447.

Septums are relatively inflexible, non-expandable, hollow structures that have a needle access portion to receive a fluid infusing needle. Septums enable fluid to flow into a tissue expander structure once the inner capacity of the septum is filled. As shown in the foregoing patents, the septum is connected to a tissue expander structure by a conduit such that fluid infused into the septum is directed by the conduit into a fluid entry port of the tissue expander chamber. The term "fluid entry port" as used herein refers to a predetermined fluid inlet opening in a tissue expander chamber to which a fluid conduit is connected.

The needle access portion of a septum usually has the capability of being resealable when an injection needle is withdrawn. The combination of a septum and a conduit for infusing fluid into a tissue expander chamber can also be used to remove fluid from the chamber.

Known tissue expansion systems often require that the septum and the conduit that connects the septum to the tissue expander prosthesis be implanted with the tissue expander prosthesis. The surgery for implanting a tissue expansion system normally includes an incision or incisions through which the implant is directed and a surgical pocket for accommodating the implant. The size of the implantation incision and pocket is generally based upon the size of the respective components of the tissue expander system. Thus a tissue expander with a septum requires a greater amount of surgery to implant than a tissue expander without a septum.

Ordinarily, the needle access portion of a septum is of substantially less size than the tissue expansion chamber and represents a relatively small target area in which to insert a needle for infusing or withdrawing fluid. Since repetitive infusions of fluid are usually required to accumulate fluid in a tissue expander chamber and accomplish a desired tissue expansion, the skin in the area of the septum often becomes sensitized due to frequent penetrations by an infusion needle in a relatively small needle penetration area. In addition, a septum can migrate from its original implant location which can lead to infusion problems. In some instances a septum will undesirably overturn making it difficult or impossible to carry out infusion. Surgical correction may thus be required for migration and overturning problems.

It is thus desirable to provide a tissue expansion device suitable for use as a mammary prosthesis and as a prosthesis in other areas of the body that does not require a septum or fluid conduit for the intake or removal of fluid, is self sealing, has a relatively large area for insertion of an infusion needle and can be implanted with a relatively small surgical incision.

OBJECTS AND SUMMARY OF THE INVENTION

Among the several objects of the invention may be noted the provision of a novel tissue expander, a novel tissue expander having an expansion chamber in which fluid can be infused or removed without a septum, without a conduit and without a special fluid entry port, a novel self-sealing tissue expander which can optionally include a fluid entry port with a closure valve for connection to a septum, a novel tissue expander with a self-sealing shell having flowable sealing material, a novel tissue expander with a self-sealing shell that is prestressed to force the flow of self-sealing material into a needle hole after a needle has been removed, a novel foldable self-sealing tissue expander prosthesis, a novel self-sealing tissue expander with a shell having a self-sealing portion and a non-self-sealing portion, a novel self-sealing tissue expander having a shell with different rates of expansibility, and a novel method of expanding tissue.

Other objects and features of the invention will be in part apparent and in part pointed out hereinafter.

In accordance with one embodiment of the present invention, the tissue expander includes a closed flexible shell that defines an internal chamber having no fluid entry port and is noncommunicable with any septum or conduit. The shell which has a self-sealing promontory portion is substantially collapsible when the internal chamber is empty and expandable upon infusion of fluid into the chamber. Fluid infusion is accomplished directly through the shell.

In another embodiment of the invention the shell has an optional fluid entry port and close off valve for connection to a septum and conduit during initial filling of the internal chamber. After initial filling of the chamber is completed the septum and conduit can be removed from the fluid entry port enabling the close off valve to close the entry port. The septum and conduit need not be implanted with the tissue expander shell.

In several embodiments the shell includes a shell wall formed of interior and exterior shell layers of relatively high durometer elastomeric material which is substantially nonflowable. At least one median layer intermediate the interior and exterior shell layers is formed of a relatively low durometer material that is substantially flowable. The flowable, relatively low durometer material operates to self seal a needle hole formed in the interior and exterior layers when the shell is penetrated by a needle for infusion purposes. Reinforcement material can be provided in one of the shell layers.

The shell can be prestressed by being turned inside out after formation. Thus the inner and outer layers exert a predetermined compressive force on the median layer to urge the flowable material in the median layer to fill the needle puncture opening or needle entry opening following needle infusion of fluid into the shell chamber.

Fluid can also be removed from the tissue expander chamber using the same type of needle that is used for fluid infusion.

The tissue expander also includes a needle stop member that prevents a syringe needle from passing directly out of the tissue expander chamber once it has accessed the chamber. The needle stop can be a flexible member so as to permit implantation of the tissue expander in a relatively small incision.

In one embodiment of the invention the inner and outer shell layers and the median layer are formed of the same type of material. However the durometer of the median layer is substantially less than the durometer of the inner and outer layers and affords the median layer with desired flowability characteristics.

In a further embodiment of the invention the median layer is formed of a material that differs from that of the inner and outer layers such as, for example, a heat cured adhesive.

In a further embodiment of the invention the median layer is a dual laminate that includes a sublayer of heat cured adhesive and a sublayer of uncured, uncatalyzed elastomeric gum.

In still another embodiment of the invention the median layer is a dual laminate that includes a sublayer of the low durometer material used in the first embodiment and a sublayer of uncured, uncatalyzed elastomeric gum.

In several embodiments of the invention the median layer flows into and fills in the needle entry puncture or opening in the inner and outer layers of the shell after an infusion needle is removed.

The self-sealing material is provided throughout substantially the entire promontory portion of the shell. Thus substantially the entire promontory portion can be used as a target area for needle infusion.

In another embodiment of the invention the shell can include a relatively stretchable portion, preferably shielded by a needle stop member. The relatively stretchable portion has greater distensibility than the self-sealing promontory portion of the tissue expander and can be of a non-self-sealing structure.

In all embodiments the shell can be reinforced with a layer of polyester mesh material or a layer of randomly oriented polyester fibers. The reinforcement layer can be provided at the median layer or at the exterior layer.

The invention accordingly comprises the constructions and method hereinafter described, the scope of the invention being indicated in the claims.

DESCRIPTION OF THE DRAWINGS

In the accompanying drawings,

FIG. 1 is a simplified schematic pictorial view showing a self-sealing tissue expander incorporating one embodiment of the invention in an implanted position and being infused with fluid;

FIG. 2 is a simplified schematic perspective view thereof;

FIG. 3 is a simplified schematic sectional view thereof in an implanted position;

FIG. 4 is a view similar to FIG. 3 during fluid infusion;

FIG. 11 is an enlarged sectional view of the embodiment of FIGS. 1-7;

FIGS. 12 and 13 are enlarged fragmentary sectional views of other embodiments of the invention;

FIG. 14 is a simplified schematic view of the flexible, foldable needle stop, showing a portion of the range of foldability thereof in dotted outline;

FIG. 15 is an enlarged fragmentary sectional view of another embodiment thereof; and, FIG. 16 is an enlarged sectional view of still another embodiment of the invention.

Corresponding reference characters indicate corresponding parts throughout the several views of the drawings.

DETAILED DESCRIPTION OF THE INVENTION

Figure 5:
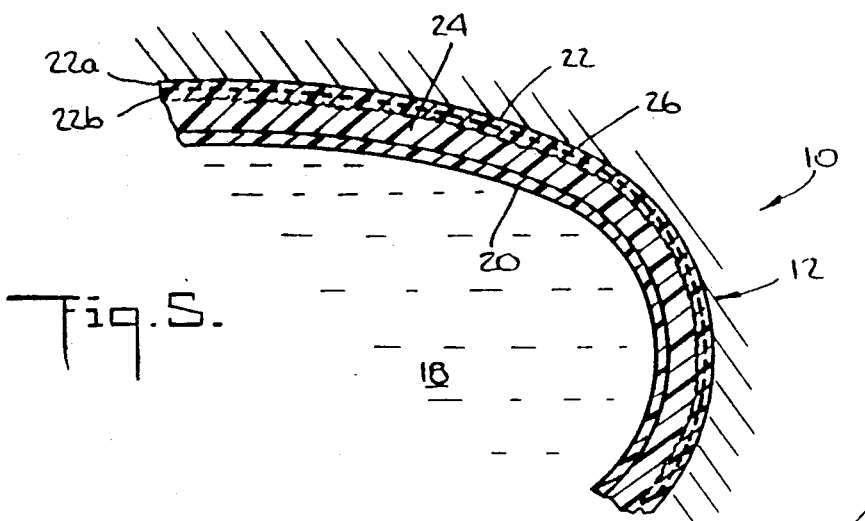
FIGS. 5-7 are enlarged fragmentary details thereof before, during and after infusion.

A tissue expander device incorporating one embodiment of the invention is generally indicated by the reference number 10 in FIGS. 1 and 2.

Referring to FIGS. 2-4, the tissue expander 10 includes a shell 12 having a base portion 14 and a dome-shaped (when expanded) promontory portion 16 joined to the base portion 14 to define a fill chamber 18. A needle stop member 40 is provided at the base portion 14 to resist needle penetration as well as prevent a needle 28 that has already entered the chamber 18 from passing outwardly of the chamber through the base portion 14. It should be noted that the tissue expander can be of any selected shape, depending upon its location and the extent of expansion desired.

Referring to FIG. 5, the shell 12 is preferably a self-sealing structure which includes inner and outer elastomeric layers 20 and 22 that can be formed, for example, of polydimethylsiloxane with a durometer of approximately 35 Shore A. The layers 20 and 22 sandwich a median layer 24 which can be formed, for example, of polydimethylsiloxane with a durometer of approximately 2 Shore A. If desired, a layer 26 of Dacron mesh can be embedded in the layer 22 in any suitable known manner. For example, the layer 22 can be composed of two sublayers 22a and 22b which sandwich the Dacron mesh layer 26. The sublayers 22a and 22b with the Dacron mesh layer 26 thus constitute the layer 22 and the shell 12 can be characterized as a tri-laminate shell.

The layers 20 and 22 are, for example, approximately 0.015 inches thick and the layer 24 is, for example, approximately 0.040 inches thick. Under this arrangement, the shell 12 will self seal a needle entry puncture 30 (FIG. 7) caused by a 21 gauge hypodermic needle 28.

It will be noted that the durometers of the various materials disclosed herein which constitute the tissue expander shell can be controlled by the extent of cross-linking of the elastomers or by the addition of reinforcing materials such as fumed silica.

Preferably the shell 12 is formed on a mandrel (not shown) having a curved surface that substantially conforms to the desired shape of the tissue expander shell 12. The sublayer 22a which is of approximate 35 Shore A durometer, is formed for example from an elastomer such as Dow Corning Q7-2245 dispersed in a suitable solvent such as Chlorothene® and coated onto the mandrel. Three coats of the elastomer at a viscosity of 30-35 seconds with a No. 3 Zahn cup have been found adequate, allowing 15 to 20 minutes of drying time between coats.

After the third coat of elastomer is dry the layer 26 of Dacron mesh is placed over the sublayer 22a. However the layer 26, before being placed on the coated mandrel, is preferably heat set to the general finished shape of the tissue expander 12.

To heat set the Dacron mesh, a piece of suitable size is stretched tight over the mandrel, held in place and baked for a predetermined time. When the mandrel is cooled to room temperature, the heat set layer 26 of Dacron mesh is placed over the sublayer 22a. Preferably the finished shape of the heat set layer 26 of Dacron mesh is slightly smaller than the finished size of the shell 12.

After the layer 26 of Dacron mesh is placed on the coated mandrel the next sublayer 22b of 35 Shore A durometer in an uncured condition is then applied over the Dacron mesh layer 26. The sublayer 22b is formed, for example, from one more coat of Dow Corning Q7-2245 elastomer, which is allowed to dry approximately 10 minutes.

The median layer 24 of 2 Shore A durometer elastomer is applied over the sublayer 22b of 35 Shore A durometer. The median layer 24 is formed, for example, from an elastomer such as Petrarch Peld-15 dispersed in a suitable solvent such as Chlorothene ®. Dow Corning Q7-2245 Part C is added and the dispersion is adjusted to a viscosity of approximately 850-950 centipoise. Four to five layers of this dispersion are next coated onto the mandrel. Thirty minutes drying time can be allowed between each coat.

After the last drying time, the elastomer layer 20 of 35 Shore A durometer, in uncured condition, is applied over the elastomer layer 24 of 2 Shore A durometer and is formed, for example, from three more coats of Dow Corning Q7-2245 elastomer dispersion coated onto the mandrel. Twenty minutes of drying time between each coat is satisfactory. After the last coat, the coated elastomer is allowed to dry further. Typical drying times are in the 10 to 15 hour range. This allows most of the solvent to dissipate and helps to prevent bubbles in the finished shell.

The sublayers 22a, 26, 22b, and the layers 24 and 20 are heat cured in a known manner. For example, the elastomer bearing mandrel is baked at 200° F. for 2 hours. After the heat curing is completed, the mandrel and the layers 20, 24 and 22, which now form a vulcanized shell, are allowed to cool to room temperature.

After cooling to room temperature, a stripping hole is cut in the bottom of the vulcanized shell while still on the mandrel (not shown). The shell is then stripped off the mandrel (not shown) and turned inside out.

Figure 6:
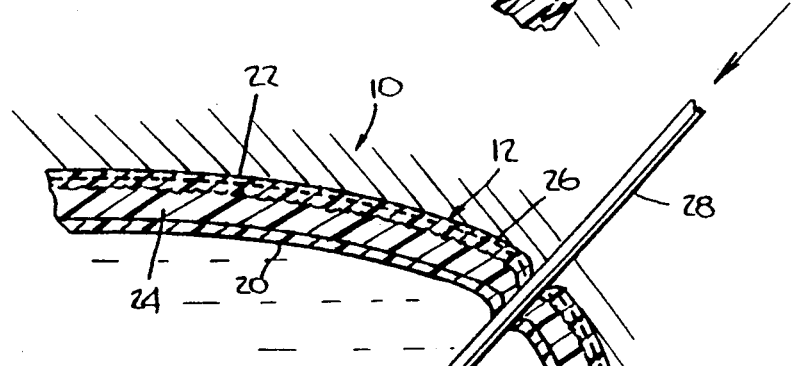
Figure 7:
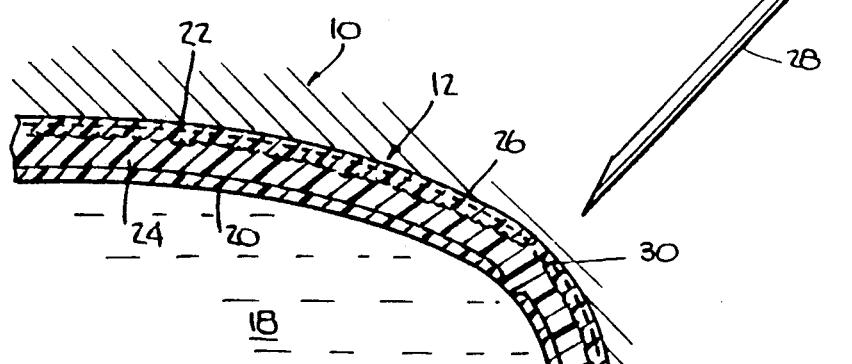

Once the shell 12 has been stripped from the mandrel and turned inside out, the layer 20 becomes the exterior layer as shown in FIGS. 5-7 and the layer 22 is the interior layer. This turning of the shell inside out places the layer 26 of Dacron mesh reinforcing material into tension and the relatively soft layer 24 into compression.

Although turning of the shell inside out is not absolutely necessary to effectuate the sealing function of the shell 12, it has been found that such procedure enhances the self-sealing characteristics of the shell. The typical shell thickness resulting from this procedure is in the range of 0.060 inches to 0.085 inches. It should also be noted that the exterior layer 22 can be provided with a higher degree of cross-linking than the interior layer 20 to exert a compression on the median layer 24.

Referring to FIGS. 3, 4 and 11, the needle stop member 40 is placed inside the shell 12 through an opening 32 (FIG. 11) left from the mandrel stripping operation.

Referring to FIG. 11, a patch 34 which can have the same tri-laminate characteristics as the shell 12 covers the opening 32. The patch 34 is secured to the base portion 14 with a suitable biocompatible adhesive such as silicone. If desired the patch 34 can be located within the shell 12 and secured to the base portion 14 from within the chamber 18.

Another patching arrangement, shown in FIG. 12, includes an inside patch 35 and an outside patch 37. The inside patch 35 includes the layers 20 and 24.

The patch layer 24 is formed by pouring an elastomer such as the Petrarch Peld-15 onto a flat aluminum disk (not shown) to an approximate dry thickness of 0.040 inches using approximately four coats of solvent-loaded material. Total dry time is approximately ten hours. The disk of elastomeric material is cured at approximately 275° F. for approximately two hours. After curing and cooling, a flat disk of unvulcanized elastomer such as Dow Corning ETR 4735 is placed on top of the Petrarch Peld-15 to form the patch layer 20. This sandwich is then baked for 15 minutes at approximately 200° F. The vulcanized patch 35 is then stripped from the flat disk mold.

The needle stop 40 is placed inside the shell 12. The vulcanized inside patch 35 is then placed inside the shell 12.

The outside patch 37 is formed with an unvulcanized Dacron mesh bearing patch of Dow Corning ETR 4735. The patch 37 is pressed over the opening 32 from the outside of the shell 12 and into intimate contact with the vulcanized patch 35. The contact between the inside and outside patches 35 and 37 is not shown for the purpose of maintaining a clarified representation of the relative arrangement of the layers 35 and 37. The assembled patch layers 35 and 37 and the shell 12 are baked at approximately 275° F. for two hours to vulcanize the patch sandwich to the shell 12.

A further optional patching arrangement is shown in FIG. 13. The needle stop member 40 is placed into the shell 12 through the opening 32. A patch 39 formed of the same material as the layer 20 is vulcanized to the outside of the shell 12 across the opening 32. Thus the shell 12 is not self sealing at the patch 39. However the opening 32 and the patch 39 are shielded by the needle stop member 40.

Since the patch 39 is not reinforced it is more stretchable and distendible than the trilaminate structure of the shell 12. The patch 39 thus permits the shell 12 to expand or stretch in the area of the patch. If desired, the patch 39 can be provided inside the shell 12.

It will be noted that FIGS. 2-4 and 16 omit the showing of a patch for purposes of simplification.

The needle stop member 40 can be freely disposed in the chamber 18 or adhered to the base portion 14 with a suitable adhesive such as a silicone adhesive of the room temperature vulcanizing type. The needle stop member 40 has a peripheral shape that substantially corresponds to the shape of the base portion 14 and is formed of a needle impenetrable, noncorrosive material such as titanium or stainless steel.

Referring to FIGS. 11 and 14, the needle stop 40 includes a main barrier section 42 of substantially uniform thickness, for example, approximately 0.002 inches, and a rolled peripheral edge or bead portion 44 which can have a roll diameter of approximately 0.060 inches. The overall diameter of the needle stop 40, for a tissue expander with a circular base portion 14, can be for example, approximately 4 inches.

The needle stop member 40 is a flexible, foldable structure and can be bent in the manner shown in FIG. 14, which shows a portion of the range of foldability of the needle stop 40. The flexibility and foldability of the needle stop 40 is due to the flexibility of the main section 42 and the resiliency of the bead portion 44, which affords the needle stop 40 with a memory that restores the needle stop 40 to an unfolded condition after a folding force is released therefrom.

In using the tissue expander 10, the fill chamber 18 is substantially empty prior to implantation. The shell 12 and the needle stop 40 can thus be compacted or folded to facilitate implantation. Folding or compaction of the tissue expander 10 helps minimize the size of an implantation incision (not shown) needed for implantation of the tissue expander 10.

After the tissue expander 10 has been implanted in a patient for use as a mammary prosthesis, for example, and the folding forces released, the needle stop 40 will unfold to the normally unfolded condition and the tissue expander 10 can be infused with fluid.

Preferably the tissue expander 10 is oriented in a position below the skin 36 wherein the needle stop 40 has a proximal location such as shown in FIGS. 3 and 4.

A syringe 50 that includes the hypodermic needle 28 is directed toward the tissue expander 10 which is generally located using palpation procedures. The needle 28 is directed into the tissue expander 10, penetrating the promontory portion 16 of the shell 12 and entering the chamber 18. The needle 28 is directed toward the base 14 of the tissue expander 10 such that a point 52 of the needle 28 can bottom against the needle stop 40.

The needle stop 40 thus prevents the needle 28 from passing out of the chamber 18 once it is directed into the chamber 18 for infusion purposes. The bead portion 44 of the needle stop 40, in addition to affording the needle stop with a predetermined resiliency, also functions to limit movement of the needle point 52 beyond the bead 44.

Deflections of the needle stop 40 by the needle 28 during infusion, due to flexibility of the needle stop 40 will substantially self correct when needle pressure is removed from the needle stop 40. The needle stop 40 is thus restorable to a substantially unfolded, undeflected condition by the resiliency of the needle stop 40 and the memory of the rolled edge or bead 44.

Infusion of fluid into the chamber 18 enables the tissue expander 10 to expand from a substantially empty condition to a predetermined filled condition over a series of periodic fluid infusions.

In carrying out an infusion, the needle 28 is directed toward the shell 12, penetrating the shell in the manner shown in FIG. 6. When infusion is completed, the needle 28 is withdrawn in the manner shown in FIG. 7.

The needle entry opening 30 in the layers 20 and 22 caused by entry and withdrawal of the needle 28 is filled by material from the median layer 24 which flows into and seals the openings 30. The median layer material 24 flows into the openings 30 because such openings are areas of relatively little resistance to the flow of the median layer material 24 and also because a compressive force is imposed on the median layer 24 by the inner and outer layers 20 and 22.

The process of turning the shell 12 inside out after it has been formed on the mandrel prestresses the shell 12.

In accordance with such prestressing the inner and outer layers 20 and 22 exert a predetermined compressive force on the median layer 24 to force the material constituting the interior layer 24 into the needle entry puncture 30 that results after the needle 28 is withdrawn following infusion of the chamber 18 as shown in FIG. 7. Further sealing enhancement is due to the compressive character of the inner layer 20 which helps force closure of the puncture site at the puncture 30.

Subsequent infusions of fluid using the needle 18 at periodic time intervals can be made at various locations in the general area of the promontory portion 16 of the tissue expander 10. Thus the needle 28 can penetrate the shell 12 at different surface locations of the shell 12 at the promontory portion 16. In each instance where a needle penetration occurs in the promontory portion 16 the puncture or needle entry opening left in the layers 20 and 22 after the needle is removed from the shell 12 is sealed by the median layer material 24 which flows into the needle entry opening.

Thus the tissue expander 10 can be infused without a septum since such infusions can be made directly into the chamber 18 through the shell 12.

Under this arrangement septums and tubes to connect the septum to the tissue expander can be omitted. Furthermore, the provision of a special fluid entry port in the tissue expander can also be omitted since fluid is infused through the shell 12 of the chamber 18 at any selected location where the needle 28 can penetrate the promontory portion 16 of the shell 12.

The self-sealing integrity of the shell 12 is normally maintained when the needle 28 is a 21 gauge needle. However the rate of fill obtainable with a 21 gauge needle may unduly prolong the inflation or filling process of the tissue expander 10. Thus if a quick fill of the tissue expander 10 is desirable at the time of implantation and use of a larger infusion needle may compromise the self-sealing integrity of the shell 12, a conventional septum, connector tube and inlet valve port (not shown) can be optionally combined with the tissue expander 10.

The septum and connection tube need not be implanted with the tissue expander 10, and when the initial inflation or initial filling of the chamber 18 is completed, the septum and connecting tube can be removed. It should be noted that the terms "initial inflation" or "initial filling" may refer to a less than full capacity inflation or filling of the chamber 18.

During initial inflation or filling the tissue expander shell 12 can thus include a conventional closure valve (not shown) or other joining arrangement at a fluid inlet port (not shown) with a conventional connection tube (not shown) joining the tissue expander shell to a conventional septum (not shown). The closure valve ensures that the tissue expander inlet port (not shown) remains closed when the connection tube is detached from the shell after the initial filling of the tissue expander 10 is completed.

Thus the self-sealing tissue expander 10 can be optionally provided with a connector valve for a septum and connection tube where quick inflation or filling is desirable. The valve and the fluid inlet port of the tissue expander shell can be entirely omitted from the tissue expander 10 when it is feasible to fill or inflate the tissue expander with a 21 gauge needle.

It is within the contemplation of this invention that periodic infusions of fluid or withdrawals of fluid from the shell chamber 18 be accomplished directly through a self-sealing portion of the shell 12.

In a further embodiment of the invention, the reinforced layer 26 of Dacron mesh such as shown in the tissue expander 10, is replaced by combining a Dow Corning Q7-2245 Chlorothene ® dispersion with polyester fibers such as Dacron in a ratio of 10:1 by weight, for example. The Dacron fibers can be, for example, ⅛ inch long and 1.5 denier. Under this arrangement there is no need to use an initial heat set of the Dacron reinforcing material before it is incorporated into the tissue expander shell. In addition, the tissue expander shell with randomly oriented Dacron fibers has greater expandability than the tissue expander shell with the layer 26 of Dacron mesh reinforcement. The randomly oriented layer of fibers can be provided at the median layer 24 or at the outer layer 22.

Figure 8:
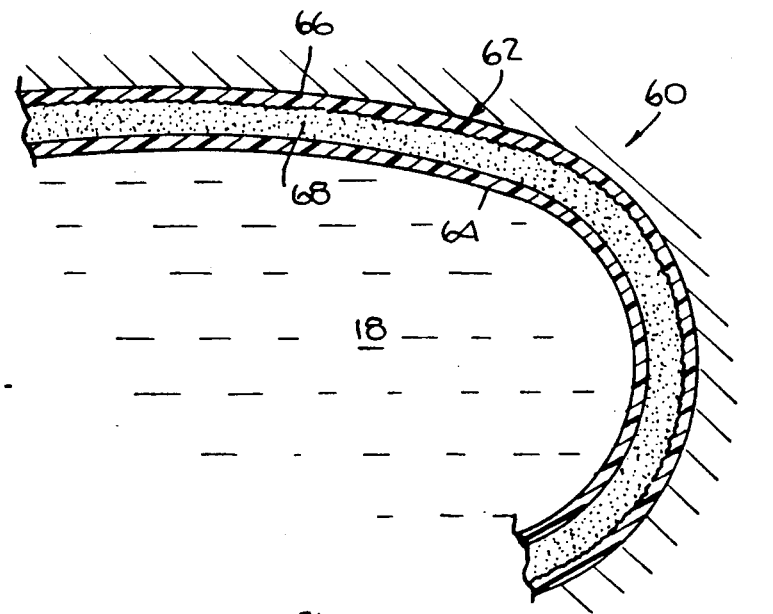
FIGS. 8-10 are enlarged fragmentary details of further embodiments thereof.

Another embodiment of the tissue expander is generally indicated by the reference number 60 in FIG. 8. The tissue expander 60 includes a shell 62 having inner and outer layers 64 and 66 which sandwich a median layer 68.

The inner and outer layers 64 and 66, which are similar to the layers 20 and 22, can be formed of polydimethylsiloxane with a durometer of approximately 35 Shore A in a manner similar to that previously described for the tissue expander 10.

The median layer 68 can be formed of a polydimethylsiloxane heat cured adhesive which possesses similar self-sealing characteristics as the relatively low durometer polydimethylsiloxane median layer 24. Thus after the layer 62 is formed on a mandrel (not shown) in a manner similar to that described for forming the layer 22, the layer 68 is formed, for example, with an adhesive such as Dow Corning 96-083 silicone adhesive applied in two to three coats, allowing 15 to 20 minutes of drying time between each coat. Next, two to three coats of a solution of Dow Corning Q7-2245, without the Part B catalyst are applied. This prevents the elastomer from vulcanizing, leaving a sticky, gummy material embedded in the shell.

The layer 64 is then formed in a manner similar to that described for forming the layer 20. The shell 62 is cured, stripped from the mandrel and turned inside out in a manner similar to that previously described for the shell 12. The shell thickness is in a similar range as the thickness of the tissue expander shell 12. Although not shown, the tissue expander 60 includes a base portion having the same characteristics as the shell 62, and a needle stop member similar to the needle stop member 40.

Although not shown, the outer layer 66 can also include a Dacron mesh reinforcement similar to the reinforcement 26. The shell 62 is prestressed in a manner similar to that previously described for the shell 12 to cause the layers 64 and 66 to exert a predetermined compressive force on the median layer 68 and the tissue expander 60 is used in a manner similar to that previously described for the tissue expander 10.

If desired, the Dacron mesh reinforcement can be placed in the mid layer 68. As previously noted, turning of the shell inside out after formation enhances the self-sealing characteristics of the shell although adequate self-sealing will result without turning the shell inside out.

Figure 9:
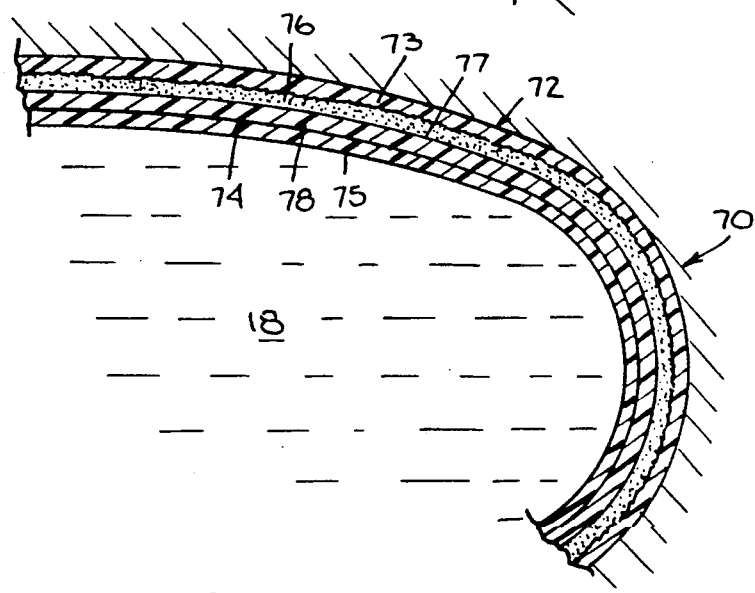

A further embodiment of the tissue expander is generally indicated by the reference number 70 in FIG. 9. The tissue expander 70 has a shell 72 with inner and outer layers 73 and 75 that are both formed in a manner similar to the layer 20 of the tissue expander 10. The shell 72 also includes a median sealant layer 74 that comprises a sublayer 76 of polydimethylsiloxane heat cured adhesive similar to the material constituting the layer 68 and a sublayer 78 of substantially uncured, uncatalyzed polydimethylsiloxane gum which can be formed, for example, of uncatalyzed Dow Corning Q7-2245 elastomer. The sublayer 78 remains substantially uncured because it is uncatalyzed.

A reinforcement layer 77, between the sublayers 76 and 78 is formed, for example, of Dacron reinforced catalyzed elastomer such as Dow Corning catalyzed Q7-2245 elastomer. The Dacron reinforcement is similar to the layer 26 of Dacron mesh.

The sublayers 76 and 78 have desired flowability and are subject to a predetermined compressive force due to the prestressing of the shell 72 in a manner similar to that described for the shell 10. The sublayers 76 and 78 are thus flowable to plug and seal the needle puncture hole 30 resulting from infusion by a hypodermic needle 28. The tissue expander 70, which also includes a base portion and needle stop similar to that disclosed for the tissue expander 10, is used in a manner similar to that previously described for the tissue expander 10.

Figure 10:
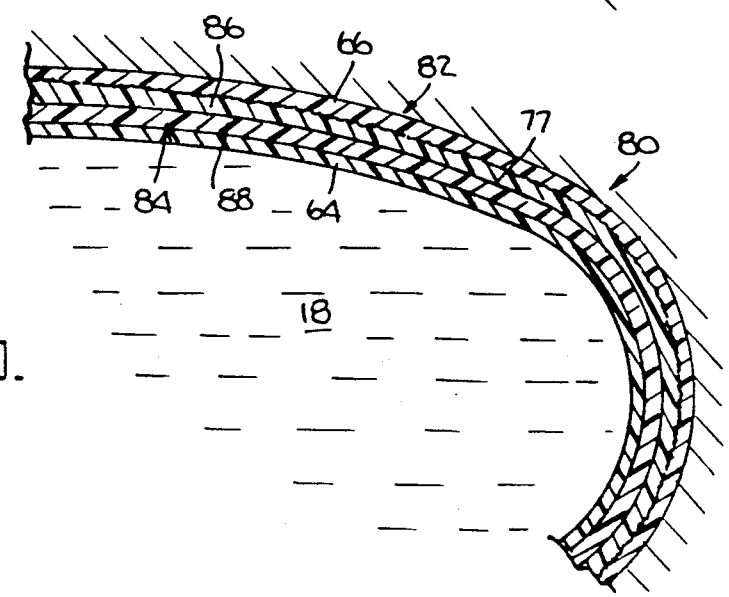

Another embodiment of the invention is generally indicated by the reference number 80 in FIG. 10. The tissue expander 80 has a shell 82 that differs from the shell 72 of the tissue expander 60 by inclusion of a median sealant layer 84 that comprises a sublayer 86 of polydimethylsiloxane of approximately 2 Shore A durometer, similar to the elastomer constituting the layer 24, and a sublayer 88 of substantially uncured, uncatalyzed polydimethylsiloxane gum similar to the elastomer constituting the sublayer 78. A reinforcement layer 77 is also provided between the sublayers 86 and 88.

The sublayers 86 and 88 have desired flowability and are subject to a predetermined compressive force due to prestressing of the shell 82 in a manner similar to that described for the shell 10. Both of the median sublayers 86 and 88 flow and plug the hole left by the hypodermic needle 28 to accomplish the self-sealing function of the shell 82 after the hypodermic needle 28 is removed following infusion. The tissue expander 80 also includes a base portion and needle stop as previously disclosed for the tissue expander 10, and is used in a manner similar to that previously described for the tissue expander 10.

If desired, an inflexible needle stop member (not shown) can be substituted for the flexible needle stop member 40 in the tissue expander 10 as well as in the tissue expander embodiments of FIGS. 8, 9 and 10.

Also, if desired, the tissue expander shell can be formed with a tri-laminate promontory portion similar to the promontory portion 16 and a bi-laminate base portion that sandwiches the needle stop 40. For example, referring to FIG. 15, a tissue expander 90 includes a shell similar to the shell 12 of the tissue expander 10 except that a base portion 92 of the shell is comprised of the inner layer 20 and the outer layer 22 of the relatively high durometer elastomer which sandwich the needle stop 40. Thus the base portion 92 can omit the median layer 24 of self-sealing elastomer incorporated in the promontory portion 16 of the shell 10. It should also be noted that the base portion of other embodiments disclosed herein can omit the self-sealing median layer whether the needle stop member is embedded in the base portion, freely disposed in the chamber or provided on the base portion as in the tissue expander 10.

A further embodiment of the tissue expander is generally indicated by the reference number 100 in FIG. 16. The tissue expander 100 includes a shell 102 identical to the shell 12 of the tissue expander 10. The tissue expander 100 also includes a needle stop member 104 that is freely disposed at the base portion 14 of the shell 102.

The needle stop 104 comprises a wire mesh insert 106 which can be formed of stainless steel. A number 80 mesh having a 0.0055 inch wire diameter has been found adequate. A plastic material such as a silicone elastomer is molded over each side of the mesh to form layers 108 and 110. The thickness of each layer 108 and 110 can be approximately 0.02 inches. A plastic bead 112 is formed at the periphery of the insert 62 as a continuation of the layers 108 and 110. The bead 112 can be approximately 0.05 inches thick and 0.250 inches wide.

The needle stop 104 can be of an selected shape such as a circular shape for example, to correspond to the general shape of the tissue expander 100 in which the needle stop is disposed. The needle stop 104 is a flexible needle stop and has similar folding and unfolding characteristics as the needle stop 40. After a folding restraint is removed from the needle stop 104 the bead portion 112 functions to help restore the normally unfolded condition. The needle stop 104 functions in a manner similar to that previously described for the needle stop 40. The tissue expander 100 also is used in a manner similar to that previously described for the tissue expander 10.

The self-sealing capability of the tissue expander shell is thus dependent on several variables, namely laminate thickness, laminate durometer, hypodermic needle diameter and laminate modulus, for example. The higher durometer elastomer that constitutes the inner and outer layers of the shell are placed on either side of the softer or lower durometer median layer elastomer in order to:

1) limit the elongation of the lower durometer material, thus preventing the stretching open of a hole through the laminate, 2) provide additional tensile strength, 3) help to provide a firmer, higher modulus material against which the softer median layer material can compress to fill any holes, and 4) provide a less tacky feel to the outside of the tissue expander shell to facilitate handling.

It has been found that lower durometer elastomers self seal better than those with higher durometers. A lower durometer elastomer is incorporated as the median laminate for this reason and because it deforms and flows under a lower compressive force. The lower durometer elastomer also has an excellent memory and tends to return to its original position after being pushed out of the way, as for example, by the point of a hypodermic needle. The lower durometer elastomer, because of its tacky nature, has the tendency to remain sealed together once it is in contact with itself. Increased pressure within the tissue expander shell such as might be attributable to the accumulation of fluid within the tissue expander chamber can also compress the median layer elastomer and enhance the self-sealing characteristics of the median layer.

It should also be noted that the durometers and thicknesses previously described for the inner and outer layers and the median layers are but one of many combinations that can be used which still meet the functional parameters required for the tissue expander device.

Some advantages of the present invention evident from the foregoing description include a tissue expander that has the capability of self sealing a puncture or needle entry opening caused by an infusion needle after the needle has been withdrawn. A prestressed shell helps urge the self-sealing material into the opening or puncture caused by an infusion needle. The self-sealing tissue expander can be implanted in a relatively small incision since a septum or a conduit which connects the septum to a tissue expander within the tissue expander system is not necessary, and if used during initial filling of the tissue expander, can be subsequently removed and need not be implanted. As a result, the implantation incision can be relatively small thereby minimizing patient discomfort and abbreviating the necessary healing time for such implantation. The self-sealing tissue expander can also be used with different types of needle stop members both flexible and inflexible, and a patch material that is more stretchable and distensible than the self-sealing portion of the shell. The self-sealing shell is thus adapted to have increased stretchability and distensibility.

In view of the above, it will be seen that the several objects of the invention are achieved and other advantageous results attained.

As various changes can be made in the above constructions and method without departing from the scope of the invention, it is intended that all matter contained in the above description or shown in the accompanying drawings shall be interpreted as illustrative and not in a limiting sense.

What is claimed is:

1. A tissue expander for implantation in a patient to promote tissue growth comprising, a closed flexible shell defining an internal chamber, said shell being substantially collapsible when said chamber is empty and expandible upon infusion of fluid into said chamber, said shell including a shell wall formed of interior and exterior shell layers of relatively high durometer elastomeric material which is substantially nonflowable, and at least one median layer intermediate said interior and exterior shell layers of relatively low durometer material which is flowable for self-sealing a needle hole formed in said interior and exterior layers of said shell wall by a needle of predetermined cross section which penetrates the interior and exterior layers of said shell wall into said chamber to inject or withdraw fluid, the durometer of said median layer material being selected to enable said median layer material to flow into and seal said needle hole in said interior and exterior shell layers when said needle is withdrawn from said shell wall.

2. The tissue expander as claimed in claim 1 wherein the median layer of low durometer material is provided at predetermined portions of said shell.

3. The tissue expander as claimed in claim 2 wherein said shell includes a promontory portion and said median layer of low durometer material is provided at said promontory portion.

4. The tissue expander as claimed in claim 1 including needle stop means disposed within said shell for stopping a needle that passes through said shell into said chamber from continuing to pass outwardly of said chamber.

5. The tissue expander as claimed in claim 4 wherein said said means for stopping a needle is a flexible and foldable needle stop member, said needle stop member being normally unfolded and having a predetermined resiliency to unfold from a predetermined folded condition to said unfolded condition after a folding restraint for holding said needle stop member in said folded condition is removed.

6. The tissue expander as claimed in claim 4 wherein said needle stop means for stopping said needle is non-foldable.

7. The tissue expander as claimed in claim 1 including means for controlling the relatively high durometer of the material forming said interior and exterior shell layers.

8. The tissue expander as claimed in claim 7 wherein the material forming said interior and exterior shell layers is cross-linked to provide said means for controlling the relatively high durometer.

9. The tissue expander as claimed in claim 7 wherein the material forming said interior and exterior shell layers includes a reinforcing material to provide said means for controlling the relatively high durometer.

10. The tissue expander as claimed in claim 9 wherein said reinforcing material is fumed silica.

11. The tissue expander as claimed in claim 1 wherein said interior and exterior shell layers are formed of polydimethylsiloxane.

12. The tissue expander as claimed in claim 1 wherein said median layer is formed of elastic polydimethylsiloxane.

13. The tissue expander as claimed in claim 1 wherein said median layer is formed of elastic polydimethylsiloxane heat cured adhesive.

14. The tissue expander as claimed in claim 1 wherein said median layer is a dual laminate.

15. The tissue expander as claimed in claim 14 wherein said dual laminate comprises a sublayer of adhesive material and a sublayer of uncatalyzed gum.

16. The tissue expander as claimed in claim 15 wherein said adhesive sublayer is polydimethylsiloxane heat cured adhesive and said gum sublayer is polydimethylsiloxane gum.

17. The tissue expander as claimed in claim 14 wherein the dual laminate is a sublayer of elastomeric material having a durometer of approximately 2 Shore A and a sublayer of uncatalyzed elastomeric gum.

18. The tissue expander as claimed in claim 17 wherein the elastomeric material is polydimethylsiloxane and the gum layer is polydimethylsiloxane gum.

19. The tissue expander as claimed in claim 7 wherein said polydimethylsiloxane is cross-linked.

20. The tissue expander as claimed in claim 18 wherein said polydimethylsiloxane elastomeric material includes a second reinforcing material.

21. The tissue expander as claimed in claim 11 wherein said second reinforcement material is fumed silica.

22. The tissue expander as claimed in claim 1 wherein said shell wall includes a first reinforcement material.

23. The tissue expander as claimed in claim 22 wherein said first reinforcement material is formed of Dacron mesh having a predetermined mesh size.

24. The tissue expander as claimed in claim 23 wherein said Dacron mesh is embedded in said exterior layer.

25. The tissue expander as claimed in claim 23 wherein said Dacron mesh is embedded in said median layer.

26. The tissue expander as claimed in claim 1 wherein said interior and exterior layer materials have a durometer of approximately 35 Shore A.

27. The tissue expander as claimed in claim 1 wherein the median layer material has a durometer of approximately 2 Shore A.

28. The tissue expander as claimed in claim 1 wherein said exterior shell layer is prestressed to exert a predetermined compression on said median layer material to force said media layer material to flow into said needle hole in said interior and exterior shell layers.

29. The tissue expander as claimed in claim 1 further including a separate and remote septum, a fluid entry port in said tissue expander shell, and a connecting tube joining said septum and said fluid entry port.

30. The tissue expander as claimed in claim 1 wherein said shell includes a first area portion which is formed of said interior and exterior shell layers and said median layer, said interior and exterior layers having respective predetermined thicknesses, and a second area portion formed of only said relatively high durometer elastomeric material having a predetermined thickness substantially equivalent to the thickness of one of said interior and exterior layers, such that said shell is relatively more stretchable and distendible at said second area portion than said first area portion in response to fluid pressure on said shell from within said chamber.

31. The tissue expander as claimed in claim 7 wherein the exterior layer material has a higher degree of cross-linking than the interior layer material to exert a compression on the median layer material.

32. The tissue expander as claimed in claim 22 wherein said first reinforcement material includes a randomly oriented array of polymeric fibers.

33. The tissue expander as claimed in claim 32 wherein said polymeric fibers are of a predetermined length and diameter.

34. The tissue expander as claimed in claim 33 wherein said fibers are in said exterior layer.

35. The tissue expander as claimed in claim 33 wherein said fibers are in said median layer.

36. A tissue expander for implantation in a patient to promote tissue growth comprising, a closed flexible shell defining an internal chamber, said shell being substantially collapsible when said chamber is empty and expandable upon infusion of fluid into said chamber, said shell being formed of a needle penetrable material and including a first area portion wherein said needle penetrable material includes a section of sealant material which is flowable for self-sealing a needle hole formed in said first area portion by a needle of predetermined cross section which penetrates said first area portion into said chamber to inject or withdraw fluid, said sealant material being flowable into said needle hole so as to seal said needle hole in said first area portion when said needle is withdrawn from said shell wall and needle stop means disposed within said shell for stopping a needle that passes through said shell into said chamber from continuing to pass outwardly of said chamber, wherein said means includes a flexible and foldable needle stop member being normally unfolded and having a predetermined resiliency to unfold from a predetermined folded condition to said unfolded condition after a folding restraint for holding said needle stop member in said folded condition is removed.

37. The tissue expander as claimed in claim 36 wherein said first area portion includes an interior and exterior layer of relatively high durometer elastomeric material which is substantially nonflowable and at least one median layer of said sealant material intermediate said interior and exterior shell layers, said median layer being of relatively low durometer elastomeric material.

38. The tissue expander as claimed in claim 36 wherein said first area portion has relatively low stretchability and distensibility and said shell includes a second area portion that has relatively high stretchability and distensibility, such that said shell is relatively more stretchable and distendible at said second area portion than said first area portion in response to fluid pressure on said shell from within said chamber.

39. The tissue expander as claimed in claim 38 wherein said first area portion is formed of interior and exterior shell layers and a median layer of said sealant material, said interior, exterior and median layers having respective predetermined thicknesses, and said second area portion does not include said sealant material and has a predetermined thickness less than the overall thickness of said interior, exterior and median layers, such that said shell is relatively more stretchable and distendible at said second area portion than said first area portion in response to fluid pressure on said shell from within said chamber.

* * * * *